United States Patent
McGinn et al.

(10) Patent No.: US 6,752,148 B1
(45) Date of Patent: Jun. 22, 2004

(54) MEDICAMENT DRY POWDER INHALER DISPENSING DEVICE

(75) Inventors: Joseph T. McGinn, Flemington, NJ (US); Suggy S. Chrai, Cranberry, NJ (US); Bogdan Brycki, Mount Laurel, NJ (US); Bawa Singh, Voorhees, NJ (US); Peter Coyle, Newton, PA (US); Gary Santonastaso, Belle Mead, NJ (US); Hoi Cheong Sun, Dayton, NJ (US)

(73) Assignee: Delsys Pharmaceutical Company, Monmouth Junction, NJ (US)

( * ) Notice: Subject to any disclaimer, the term of this patent is extended or adjusted under 35 U.S.C. 154(b) by 0 days.

(21) Appl. No.: 09/623,937
(22) PCT Filed: Feb. 10, 1999
(86) PCT No.: PCT/US99/02869
§ 371 (c)(1), (2), (4) Date: Sep. 1, 2000
(87) PCT Pub. No.: WO99/44663
PCT Pub. Date: Sep. 10, 1999

(51) Int. Cl.[7] .................. A61M 15/00; A61M 16/00
(52) U.S. Cl. .................. 128/203.15; 128/203.19
(58) Field of Search ........... 128/203.15, 203.12, 128/203.19, 203.21, 200.14, 200.17, 200.21, 200.23, 200.12; 604/58; 222/160

(56) References Cited

U.S. PATENT DOCUMENTS 4,203,454 A * 5/1980 Wutscher ............... 128/203.12
5,437,271 A * 8/1995 Hodson et al. ......... 128/203.15
5,469,843 A * 11/1995 Hodson ................. 128/203.21
5,619,984 A * 4/1997 Hodson et al. ......... 128/200.16
5,655,523 A * 8/1997 Hodson et al. ......... 128/203.15
5,740,793 A * 4/1998 Hodson et al. ................. 221/5
6,029,663 A * 2/2000 Eisele et al. ........... 128/203.21

FOREIGN PATENT DOCUMENTS

WO WO90/13328 11/1990
WO WO93/09832 5/1993
WO WO97/25086 7/1997

* cited by examiner

Primary Examiner—Henry Bennett
Assistant Examiner—Sabrina Dagostino
(74) Attorney, Agent, or Firm—Carella, Byrne, Bain, Gilfillan, Cecchi et al.; Elliot M. Olstein; William Squire

(57) ABSTRACT

An inhaler disc cartridge comprises a carrier disc with radially outwardly extending resilient fingers, each with a medicament powder dosage. A sealing disc and an indexing ring are bonded to the disc. A cam sequentially and manually deflects a selected finger causing it to snap against an anvil to release the dosage by momentum energy transfer. In other embodiments, a cassette includes a carrier substrate reel of deposited powder dosages with a dosage sealing tape. The substrate comprises a belt with a plurality of transversely extending triangular fingers, each finger tip with a dosage thereon. Each finger is snapped in sequence against an anvil while a clamp secures the belt as the fingers are deflected. The spring fingers are corrugated in one embodiment cooperating with an anvil having channels and a device for inducing agglomeration breakup air streams through the channels. Other embodiments are for impact deflection of a dosage carrying substrate in a cartridge or cassette against an anvil to release the dosages.

27 Claims, 8 Drawing Sheets

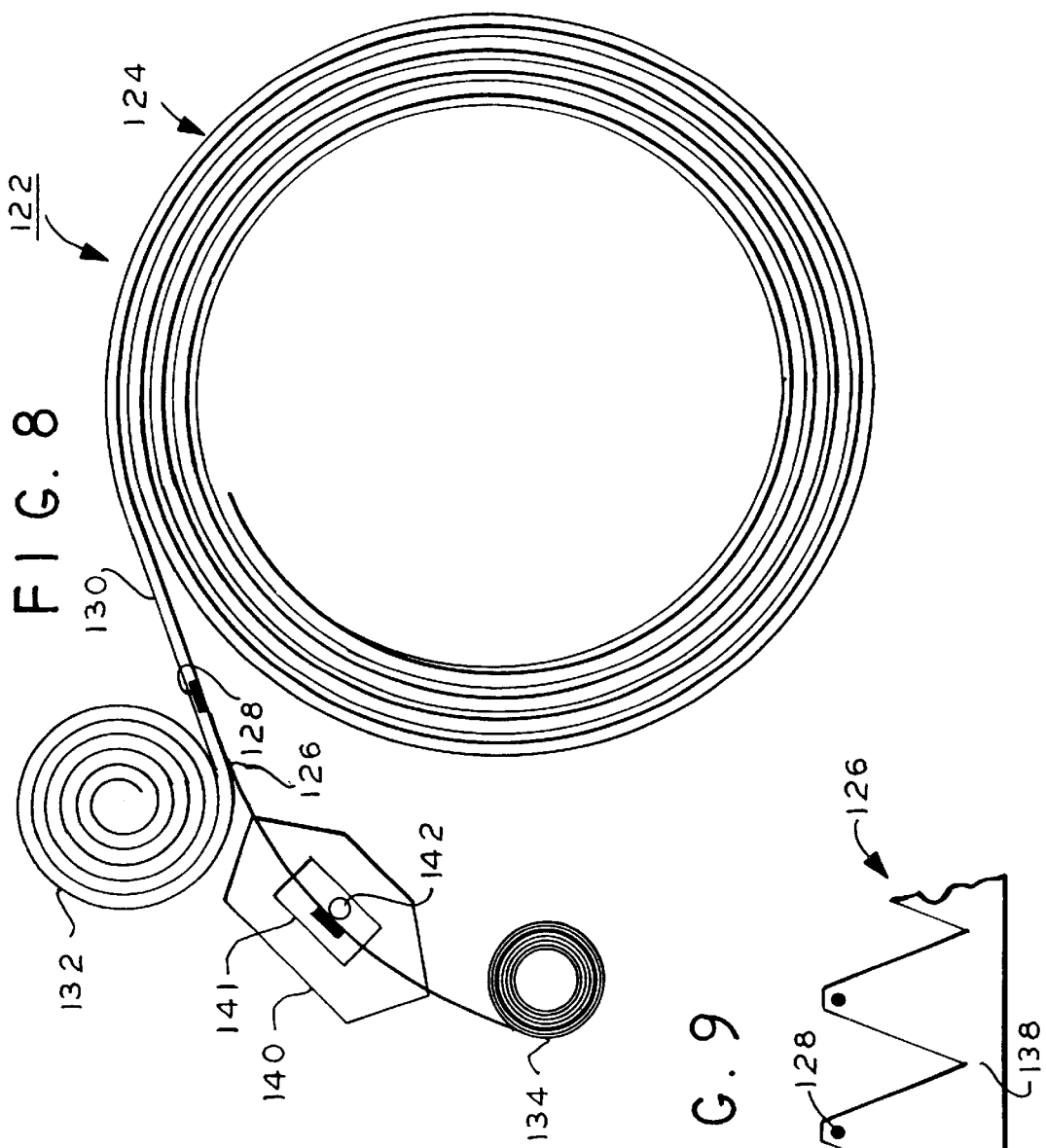
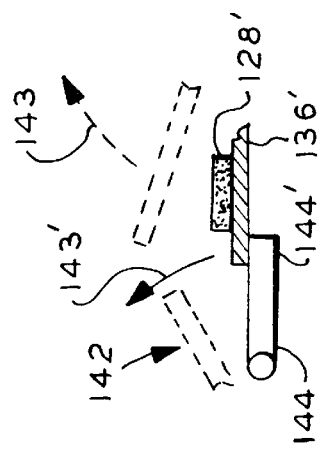
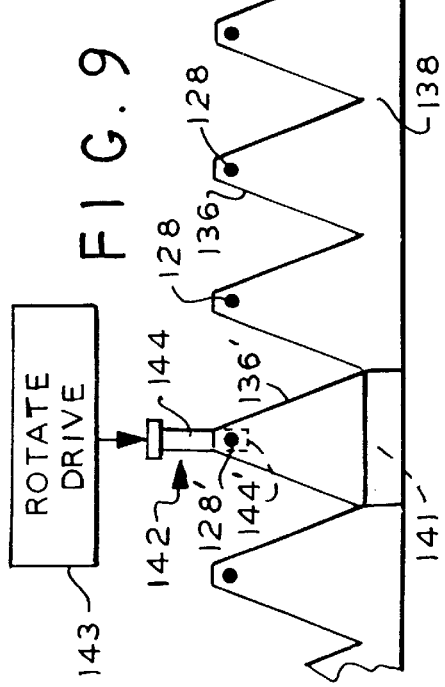

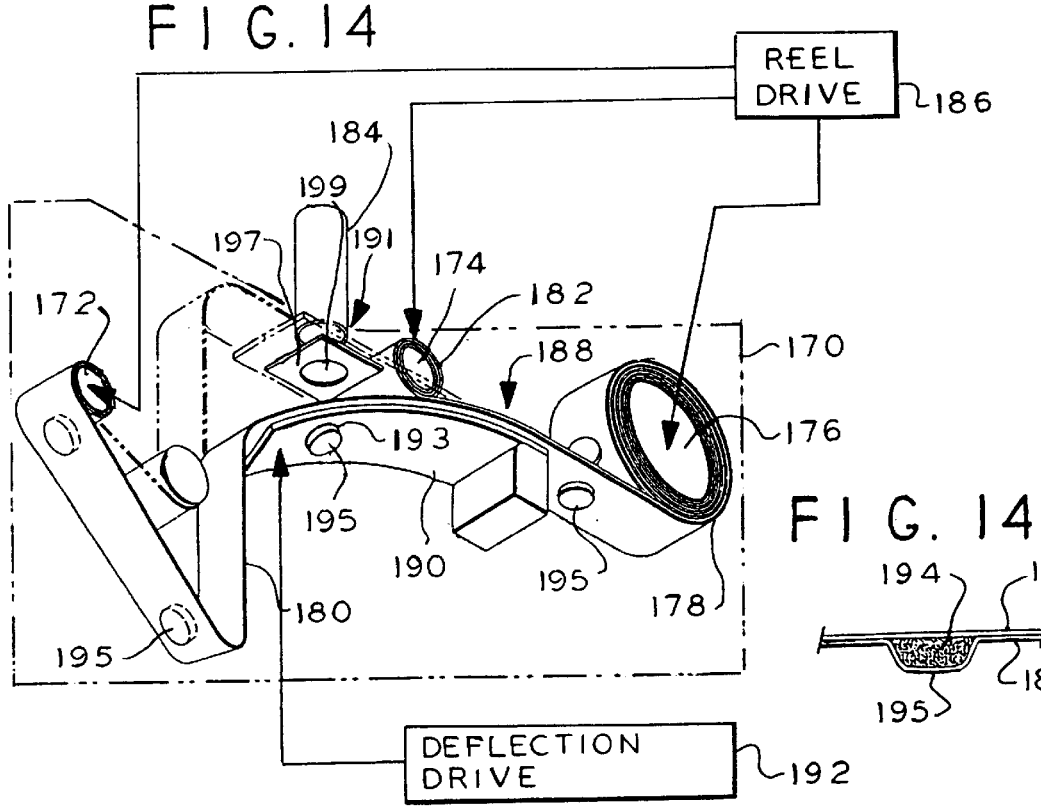
FIG. 14
FIG. 14a
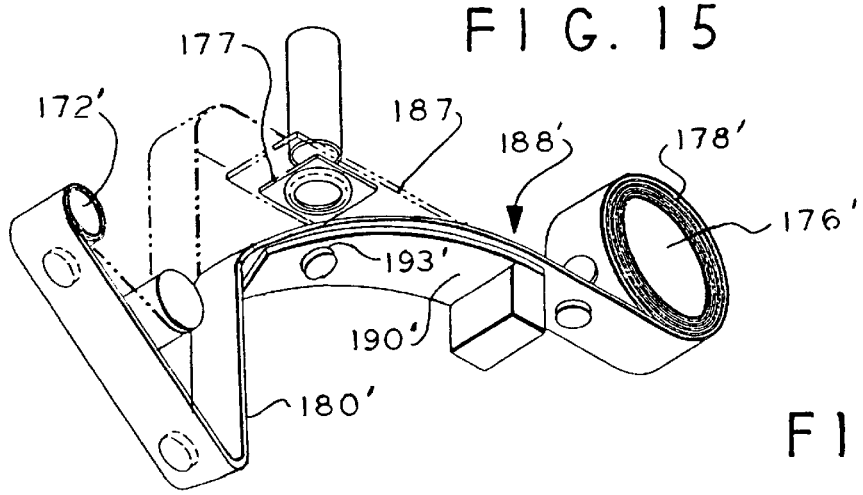
FIG. 15
FIG. 15a
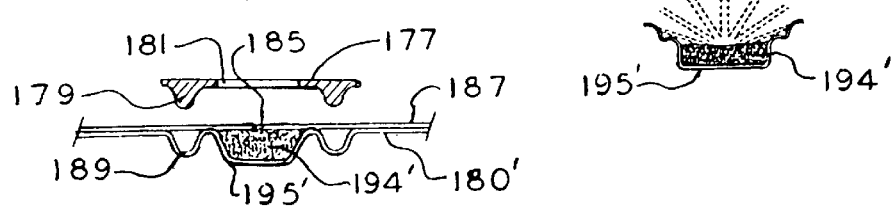
FIG. 15b

MEDICAMENT DRY POWDER INHALER DISPENSING DEVICE

Of interest are co-pending application Ser. No. 08/661,213 (PCT/US97/10162) entitled Inhaler Apparatus with Modified Surfaces for Enhanced Release of Dry Powders filed Jun. 10, 1996 in the name of Datta et al., Inhaler Apparatus with an Electronic Means for Enhanced Release of Dry Powders Ser. No. 08/661,212 filed Jun. 10, 1996 in the name of Sun et al. (PCT/US97/10162), Ser. No. 08/932,489 (PCT/US98/19228) entitled Dry Powder Delivery System filed Sep. 18, 1997 in the name of Leedom et al., Ser. No. 08/467,647 entitled Apparatus for Electrostatically Depositing and Retaining Materials Upon a Substrate filed Jun. 6, 1995 now U.S. Pat. No 5,669,973, Ser. No. 08/506,703 entitled Inhaler Apparatus for Using a Tribo-Electric Charging Technique filed Jul. 25, 1995 now U.S. Pat. No. 5,642,727, Ser. No. 08/659,501 entitled Methods and Apparatus for Electrostatically Depositing a Medicament Powder Upon Predefined Regions of a Substrate filed Jun. 6, 1996 in the name of Pletcher et al. now U.S. Pat. No. 6,007,630, Ser. No. 09/095,246 entitled Dry Powder Deposition Process filed Jun. 10, 1998 in the name of Poliniak et al. now U.S. Pat. No. 6,063,194, all of the foregoing being commonly owned; and Ser. No. 09/095,616 entitled Pharmaceutical Product and Method of Making filed Jun. 10, 1998 in the name of Chrai et al. now U.S. Pat. No. 6,303,143, the latter application being commonly owned with the assignee of the aforementioned foregoing applications and with the assignee of the present invention, and U.S. Pat. Nos. 5,714,007, 5,642,727, 5,669,973 commonly owned with the aforementioned foregoing applications. All of the aforementioned are incorporated by reference herein in their entirety.

This invention relates to inhalers for medicaments, and more particularly, to inhalers with arrangements for breaking up agglomerates of dry powder.

In addition, of interest are PCT applications WO 90/13328 and WO 93/09832. These latter applications disclose various inhaler embodiments including impact release of medicament dosages. However, these embodiments involve relatively complex camming and similar arrangements which are costly to implement. These latter applications are also incorporated by reference herein.

Dry powder inhalers are used as drug delivery devices for administering pharmaceutical compounds to individuals. Some of these devices employ a pharmaceutical powder deposited on a substrate surface and sealed with a sealing layer. In other devices, the powder may be supplied in a reservoir and then transferred to a dose carrier one dose at a time. The substrate may be provided as a tape on a reel in cassettes or in cartridges, for example. When the patient requires medication, the ideal dry powder inhaler forms a fine particle cloud that is to be inhaled and thereby delivers a high respirable fraction of the stored dose deeply into the patients lungs. In most cases, the deep recesses of the lung is the desired site for the drugs in the inhaled powder cloud.

This can be most efficiently achieved by:
1. Releasing a high fraction of the deposited drug and
2. Insuring that the powder cloud consists of individual particles or particle aggregates between 1 $\mu$m and 5 $\mu$m.

As individual particles are reduced below 10 $\mu$m, both release and particle aggregation become a serious hindrance to delivering a high respirable fraction deeply into the patient's lungs.

A common problem addressed by various prior art inhaler apparatuses for dispensing dry powder medicaments is providing for a controlled reliable release of the medicament. The dry powder medicaments inhalers may be loaded with medicaments by filling techniques not involving electrostatics. In certain other implementations, the deposited powder tends to form agglomerated particles resulting in uncontrolled variation in the amount of medicament released. Several of the aforementioned applications provide various solutions to this problem.

Numerous approaches have been taken in the design of dry powder inhalers. In some cases, the powder is released by impact of a substrate powder carrier, as disclosed in WO 93/09832. Of interest is an inhaler as disclosed in WO 90/13328.

In copending applications Ser. Nos. 661,213 and 661,212, indentations or raised surfaces are disclosed in the inhaler interior surfaces having contact with the medicament for inhalation, the surfaces minimizing the area of contact between the medicament and the surfaces of the inhaler apparatus, promoting the release of the medicament from the inhaler.

When particles of medicament agglomerate, they impact the mouth and throat rather than remain in the air flow for deposition in the lungs. One remedy is to provide tortuous channels in the inhalers to promote deagglomeration. However, the medicament may be deposited along the channels leading to inaccurate dosage dispensing. Agglomeration also results in the inhaler tending to dispense the medicament inaccurately so that greater or lesser amounts are dispensed.

The small particle size, e.g., 2 $\mu$m to 7 $\mu$m, required for transport to the lung presents a number of problems for release by the inhaler and delivery to deep lung regions. As the particle size decreases, the relative bonding force between the particle and other objects increases. This applies to both particle-to-substrate bonding and particle-to-particle bonding. As a result, particle aggregates become more tightly bound and individual particles more difficult to remove from the substrate. Aggregation increases the effective size of the drug released and diminishes the respirable fraction. The increase in relative particle-to-substrate bonding makes drug release more difficult and also decreases the respirable fraction.

Additional investigation using ultrasonic frequencies to agitate the surfaces have been unsuccessful in removing particles below 10 $\mu$m from a planar surface. There is a mismatch between the particle size and the wavelength of the substrate material in typical polymeric materials. The wavelengths of the material are a large multiple of the dimensions of the particles and does not provide efficient energy coupling. Acoustic frequencies above 100 MHz would be required for particle resonance to occur. Thus, either unrealistically high frequencies to minimize wavelength or high acoustic amplitudes to increase the force differential across the small particles are required.

The present inventors recognize a need for a drug inhaler delivery system for dry powder pharmaceutically active ingredients for breaking up such particle aggregation should they form. They recognize a need for delivery of microgram depositions in quantities ranging from about 10 $\mu$g to the milligram range with a delivery accuracy of about 10%.

A medicament powder delivery device according to the present invention comprises a carrier having at least a flexible portion on which portion is deposited a discrete medicament dosage and means for imparting an energy pulse to the carrier flexible portion for deflecting the carrier portion and releasing the dosage from the deflected portion by momentum transfer.

In one aspect, the means for imparting an energy pulse comprises means for flexing and snap releasing the flexed carrier portion.

In a further aspect, the carrier portion includes a finger resiliently extending from a carrier base region, the means for imparting for flexing the finger relative to the base region.

In a further aspect, a body is included with a cavity for receiving the carrier portion and the means for imparting including an anvil with a bore therethrough fixed to the body in the cavity for receiving the snap released finger, the bore for receiving the released dosage, and including means for causing the finger to resiliently impact the anvil to rapidly decelerate the finger to provide the momentum transfer to the dosage.

In a further aspect, the dosage tends to form aggregates, the anvil including at least one channel, further including means coupled to the housing for creating an air jet stream through the at least one channel to disintegrate aggregations of the dosage during the impact.

In a further aspect, the finger is corrugated.

In a still further aspect, the finger extends in a given direction from the base region, the finger having corrugations extending along the given direction.

The means for creating the jet stream may include a further resilient finger overlying the carrier finger for initial resilient displacement coincident with initial displacement of the carrier finger, the displaced fingers for snap release in a second displacement, the further finger for creating the air stream during the second displacement.

In a further aspect, the further finger has a different spring constant than the carrier finger so as to accelerate slower than the carrier finger upon the snap release.

In a still further aspect, the carrier includes a first disc with a plurality of radially extending fingers, a dosage on each finger, and the means for imparting comprises cam means for snap flexing a selected finger to release the dosage on the selected finger.

Index means are preferably included for indexing the selected finger to a medicament release position for snap flexing the selected finger by the cam means.

The first disc may include a carrier disc with a plurality of first fingers each carrying a dosage, a spacer disc overlying the carrier disc with a plurality of second fingers overlying and corresponding to the first fingers and a ring with index holes and a third plurality of fingers over lying and corresponding to the first and second fingers, the spacer disc being bonded to the carrier and ring discs, the indexing means for selectively engaging the ring index holes.

Cam means are preferably provided for manually flexing the selected fingers.

The cam means may flex the first and second fingers past the third fingers.

In a further aspect, the carrier comprises a belt portion with a plurality of fingers extending transversely from the belt portion, each of the fingers having a separate dosage and arranged for selective resilient displacement relative to the belt portion.

In a still further aspect, drive means are included for displacing the belt to increment the fingers sequentially to a dosage release position.

The means for imparting may include a clamp for clamping the belt portion adjacent to a given finger and a deflecting member for selectively flexing and snap releasing the selected given flexed finger relative to the belt portion.

The carrier may comprise an element, the dosage comprising a plurality of discrete dosages in spaced relation on the element, the means for imparting including a carrier deflection member adjacent to the element, and means for momentarily bending and deflecting the element to momentum transfer release a selected dosage from the element upon release of the deflected element.

In a further aspect, means are included for selectively aligning successive dosages on the element to the deflection member.

In a further aspect, a core member is included and rotatable about an axis, the element comprising an array of fingers radially extending from the core member about the core member in a spiral about the axis, means selectively align and deflect each the finger to snap release a selected dosage from the selected finger by momentum transfer.

In a further aspect, the carrier comprises a spring finger for receiving a dosage and dosage substrate from a plurality of dosages and dosage substrates in a stack aligned one over another, and means are included for selectively placing successive dosages and dosage substrates on the carrier, the means for imparting including means for snap deflecting said finger against an anvil.

IN THE DRAWING

FIG. 1 is a side elevation sectional view of an inhaler according to one embodiment of the present invention with the inhaler housing open for receiving a pharmaceutical powdered dosage carrying substrate cartridge with the cartridge installed;

FIG. 2 is a plan sectional view of the inhaler of the embodiment of FIG. 1;

FIG. 3 is a plan exploded view of the substrate cartridge for the embodiment of FIG. 1;

FIG. 3*a* is a fragmented sectional side elevation view of the assembled substrate cartridge of FIG. 3;

FIG. 3*b* is a fragmented sectional side elevation view of an alternate embodiment for the cartridge of FIG. 3*a;*

FIG. 4 is a side elevation view of a cam and lever employed in the embodiments of FIG. 1;

FIGS. 5–7 are side elevation sectional views of the inhaler of FIG. 1 showing various stages of release of the deposited dry powder medicament;

FIG. 8 is a diagrammatic side elevation view of a second embodiment of an inhaler apparatus without the housing or operating mechanism illustrating the medicament carrying substrate and dosage thereon;

FIG. 9 is a plan view of a portion of the substrate of FIG. 14;

FIG. 10 is a schematic diagram of an actuator for use in deflecting the fingers in the embodiment of FIGS. 8 and 9;

FIG. 11 is diagrammatic perspective view in more detail of a dry powder substrate for use in different embodiments herein;

FIG. 12 is an isometric fragmented view of a further substrate embodiment according to the present invention for use with the substrate embodiment of FIG. 11;

FIG. 13 is a side elevation fragmented sectional view of a further embodiment of a substrate and medicament for use in the embodiment of FIGS. 11 and 12;

FIG. 14 is a diagrammatic isometric view of a cassette embodiment for use in an impact inhaler;

FIG. 14*a* is a side elevation sectional view of the substrate for use in the embodiment of FIG. 14;

FIG. 15 is a diagrammatic isometric view of a second cassette embodiment for use in an impact inhaler;

FIG. 15*a* is a side elevation sectional view of a portion of the substrate and the anvil used in the embodiment of FIG. 15;

FIG. 15b is a side elevation view similar to that of FIG. 15a but after the substrate is impacted;

Figure 1:
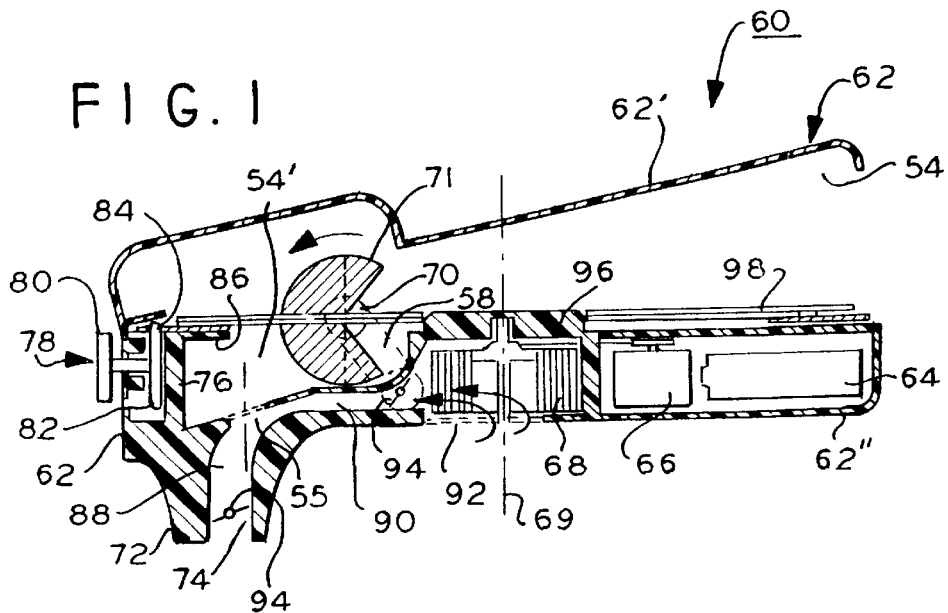

Dry powder medicament particles forming unit dosages may be charged with a given polarity in a conventional charging mechanism such as tribo-electric chargers, induction charging and so on. The particles are deposited in controlled amounts on a substrate wherein the amount of active pharmaceutical ingredients deposited at each of a plurality of locations on the substrate does not vary from a predetermined amount by more than about 5%, for example.

Reference is made to application Ser. No. 09/095,246 entitled Dry Powder Deposition Process filed Jun. 10, 1998 in the name of Poliniak et al., now U.S. Pat. No. 6,063,194, and Ser. No. 09/095,616 entitled Pharmaceutical Product and Method of Making filed Jun. 10, 1998 in the name of Chrai et al., now U.S. Pat No. 6,303,143, noted in the introductory portion and incorporated by reference herein in their entirety. These applications disclose apparatus and processes for electrostatically depositing pharmaceutically active ingredient medicaments on a substrate including charging a dry powder medicament and electrostatically attracting the charged powder particles to a substrate. In particular, the medicament is deposited in controlled amounts at discrete locations on the substrate wherein the amounts deposited do not vary from a predetermined amount by more than 5%, for example. This process is preferred.

However, other processes for electrostatically depositing dry powder medicaments on a substrate are also disclosed in the aforementioned copending applications and patents noted in the introductory portion, all of which are incorporated by reference herein. Those processes disclose electrostatically depositing controlled amounts of dry powder medicaments on a substrate at discrete locations on the substrate. Variations of the disclosed processes herein may be employed to adapt those processes to a metal or non-metallic substrate. The substrate may be a tape, a strip or disk, for example, among other shaped substrates with or without resilient fingers. Medicaments are deposited on the fingers as will be described below as employed in certain of the present embodiments. Such depositions of dry powder particles on the various substrates as described hereinbelow are within the skill of those of ordinary skill in this art.

Particle removal from surfaces tends to be more difficult as particle size decreases. This is roughly a consequence of the adhesion force decreasing more slowly than the volume and surface area as a particle's size decreases. Since the volume and surface are generally related to removing forces and deaggregation, these forces become increasingly difficult to overcome as the particle size decreases.

Forces of adhesion and agglomeration caused by van der Waal's force increase as the area of contact between a particle and substrate or between two particles increase.

To obtain high respirable fractions, electrostatic deposition is preferred to minimize particle-substrate and particle-particle contact which minimizes adhesive and agglomeration forces respectively. Also, similarly charged particles will repel one another to further minimize agglomeration.

The substrates in the inhalers described below may be either metal, e.g., stainless steel, or non-metallic as known in this art and may be of any material suitable as a medicament substrate. Non-metallic substrates are selected to have the desired mechanical flexure properties in certain of the described embodiments, for use in the disclosed impact arrangements. The selection of a substrate material depends upon a given implementation as discussed later herein in connection with the various embodiments.

To effectively form a powder cloud for inhalation, the rudimentary particle must generally be below about 6 $\mu$m and large agglomerates disrupted if they form. For low dosages, sufficiently sparse drug layers can be deposited such that particle-particle interaction is minimal or the agglomerates that form are sufficiently small to reach the targeted region of the respiratory track.

For higher dosages of drugs, aggregates will form on the substrate. These aggregates can be disrupted by the application of energy during the process of dislodging the drug and/or through the exposure of the released aggregates to a sufficiently high gas velocity. The gas exerts a differential force across the aggregates due to differences in aerodynamic drag. These differences can arise due to either a gradient in the gas velocity or geometrical differences across the aggregate.

Figure 2:
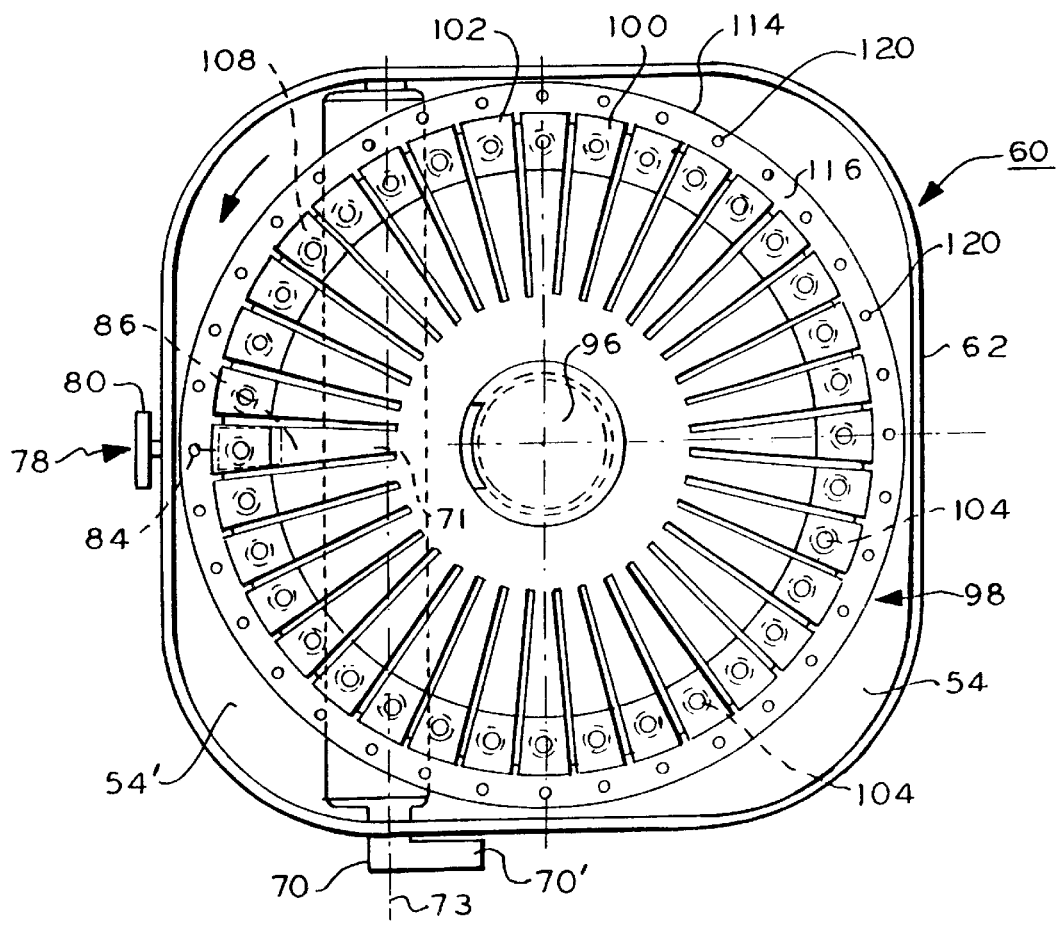

In FIG. 1, inhaler apparatus 60 includes a housing 62 defining a chamber 54 and a dispensing chamber 54'. A battery 64, a motor 66 energized selectively by the battery through a switch not shown, and a fan belt 68 driven about axis 69 by the motor 66 are located within the chamber 54. A manually operated lever 70 with a cam 71 is rotatably secured to the housing 62. The lever 70 and cam 71 pass through the chamber dispensing 54'. Lever 70 rotates about axis 73 (FIG. 7) and passes through the chamber 54. The lever has a manually operated knob 70', FIG. 2. The cam 71 is integral and one piece with the lever 70 which may be molded thermoplastic. The cam 71 is located within the chamber 54.

Figure 4:
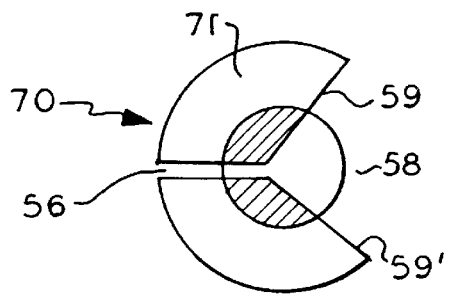

In FIG. 4, the cam 71 has a slot 56 and an ingress opening 58. Opening 58 comprises two surfaces 59 and 59' spaced at 90° and symmetrical relative to the plane of the slot 56. Opening 58 has its normal quiescent position as shown in FIG. 1 with the slot horizontal and the surfaces 59 and 59' each 45° to the horizontal.

The housing 62, FIG. 1, is preferably a clam shell comprising two halves 62' and 62" hinged at one end with a preferably living hinge and is molded one piece thermoplastic. The housing includes an integral one piece molded mouthpiece 72 attached to lower half 62". The mouthpiece 72 has an exit port 74 in fluid communication with the dispensing chamber 54' through opening 55. A support 76 is in the dispensing chamber 54'. A manually operated indexing device 78 is at the housing front. The indexing device 78 includes a knob 80 external chamber 54' and an index wheel 82 in the chamber 54' adjacent to the support 76. The index wheel 82 is rotatably secured to the housing 62 half 62" and includes an annular array of angularly spaced indexing pins 84. An optional thermoplastic member 86 is cantilevered from the support 76 in the drug dispensing chamber 54', FIGS. 1 and 2. The member 86 may be flat or arcuate. If flat it is resilient. If arcuate it may be rigid and curves downwardly as shown, FIG. 5. The member 86 may be made of other materials if desired.

The mouthpiece 72 has a dispensing chamber 88 in fluid communication with the chamber 54' through the opening 55. The chamber 88 is fluid coupled through a channel 90 to air inlet port 92. Air flow actuated butterfly valves 94 are in channel 90 and chamber 88. The housing includes a spindle 96 for receiving a drug delivery disc substrate assembly 98. The received disc 98 is rotated about the spindle 96 by the indexing device 78.

Figure 3:
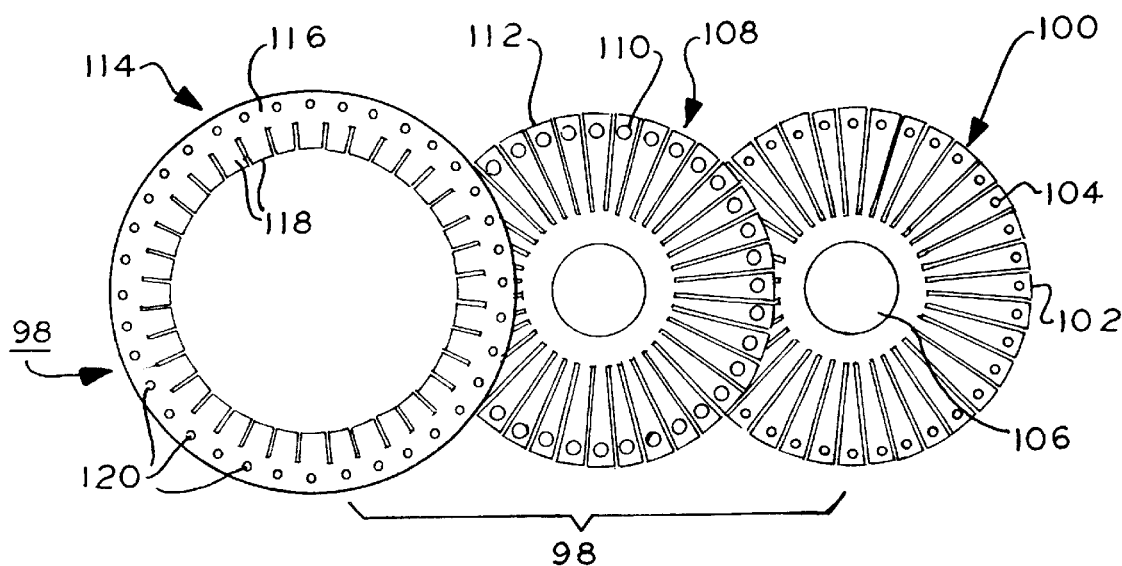
Figure 3A:
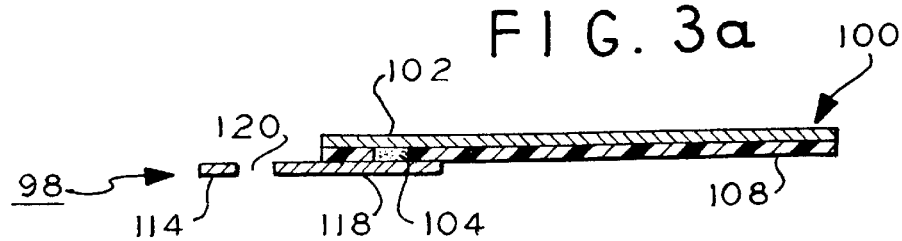

The substrate disc assembly 98, FIGS. 3 and 3a, forms a dosage cartridge. Assembly 98 comprises a multilayer circular disc including a spring metal, for example, leaf spring, dosage carrying disc 100. The disc 100 has an annular array of radially outwardly extending leaf spring fingers 102 which are resilient in a direction normal to the plane of the disc 100. A medicament dosage 104 as described previously hereinabove is deposited as described on a broad surface of each of the dosage carrier fingers 102 at their extended end region. The disc 100 has a central opening 106 for receiving the spindle 96, FIGS. 1 and 2.

Overlying the disc 100 is a spacer (or sealing layer) disc 108. Disc 108 serves to separate the substrate disc 100 from overlying sealing ring 114. In the alternative, the disc 108 may also serve as a sealing layer. Disc 108 may be spring metal or thermoplastic and has holes 110 in this embodiment for receiving therein the respective dosages 104 on the disc 100.

Figure 3B:
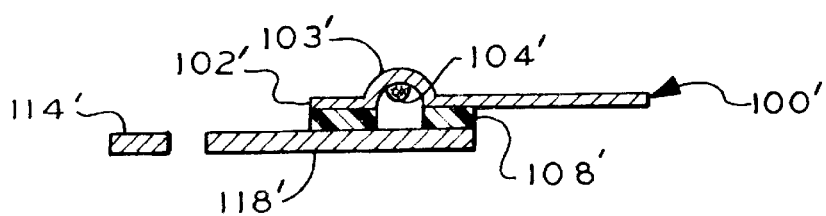

In the sealing layer embodiment, the substrate disc 100 has pockets each for receiving a corresponding discrete dosage. The disc 108 is planar and overlies the disc 100. This is shown, for example in FIG. 3b. In FIG. 3b, disc 100' comprises spring fingers 102' each having a dosage receiving dimple or pocket 103'. A separate discrete medicament dosage 104' is in the pocket 103'. The sealing disc 108' has openings 110 at the pocket 103' for spacing the dosage 104' from the ring 114' finger 118'. The disc 108' seals the dosage and is generally planar. When the disc 108' is removed from the disc 100' to release the dosage, the dosage 104' remains in place in the pocket 103 rather than possibly removed with the sealing disc 108' spaced from the dosage.

Disc 108, FIG. 3, also has a central opening and fingers 112 corresponding to and overlying the respective opening 106 and fingers 102 of disc 100. Disc 108 bonds the disc 100 thereto employing a conventional bonding agent for this purpose.

An indexing and sealing ring 114 overlies the disc 108 annular peripheral region. Ring 114 has a larger diameter than discs 100 and 108 so that an annular portion 116 extends radially outwardly of the underlying juxtaposed fingers 102 and 112 of the respective discs 100 and 108. A plurality of radially inwardly extending fingers 118 overly the outer peripheral ends of the underlying fingers 102 and 112 of respective discs 100 and 108. A circular array of disc indexing apertures 120 are in the ring 114 radially outwardly of the fingers 118. The apertures 120 selectively engage the indexing pins 84 of the indexing device 78, FIG. 1, one at a time.

The discs 100, 108 and the fingers 118 of ring 114 are bonded together in a laminated structure by a conventional adhesive bonding agent forming the cartridge disc assembly 98.

Means are provided for selectively placing and aligning successive dosages on an element to a deflection member, for example, such as by using indexing device 78, FIG. 1, indexing pins 84 which selectively engage apertures 120 of ring 114 in the received disc assembly 98 by manual rotation of the knob 80. The pins 84 place an overlying set of fingers 102, 112 and 118 of the assembly 98 aligned with and overlying the member 86. The ring 114 peripheral region 116 with the holes 120 are over the support 76 and member 86. The spindle 96 receives the disc assembly 98 at opening 106.

In operation, apparatus 60 provides a drug removal method that imparts an energy pulse for momentum transfer to the deposited powder through an impact mechanism for both low and high dosages. The disc assembly 98 is placed in operative position, FIG. 1, and the housing 62 chamber 54 is then closed, FIG. 5. In this position, the cam 71 surfaces 59 and 59' are each 45° to the plane of the assembly 98 which passes through the slot 56. When a switch, not shown, is activated, the motor 66 operates the fan 68. This starts an air flow through the channel 90 via input port 92 and exits port 74 opening the butterfly valves 94.

The extended tips of the fingers 102 and 112 may overlie the support 76 and also overlie the member 86 therebelow. The ring 114 is lowermost with the dosage facing downwardly toward the opening 55. In this orientation, the other fingers 112 and 102 are over the ring fingers 118 with the dosage finger 102 uppermost. Means are provided for flexing a finger relative to the base region and snap releasing the flexed finger relative to the base region for imparting the energy pulse noted above. For example, lever 70 and cam 71 are used to flex the fingers wherein lever 70 is manually rotated rotating the cam 71, forming a cam means, in the directions of the arrows in the sequence from FIG. 5 to FIG. 7. The cam 71 grips one set of aligned overlying fingers 102 and 112 of the disc assembly 98 that is aligned therewith and with the member 86.

As the cam 71 rotates, it also rotates and bends the aligned fingers 102 and 112, but not the ring 114 or its fingers, on the support 76. The downward flexing of the disc assembly 98 by the cam 71 flexes the two fingers 102 and 112 downwardly. These fingers then flex downwardly the aligned ring 114 finger 118 and the member 86, FIG. 5.

The member 86 assists in optimizing the shearing action between the ring 114 and the fingers 102 and 112.

Figure 5:
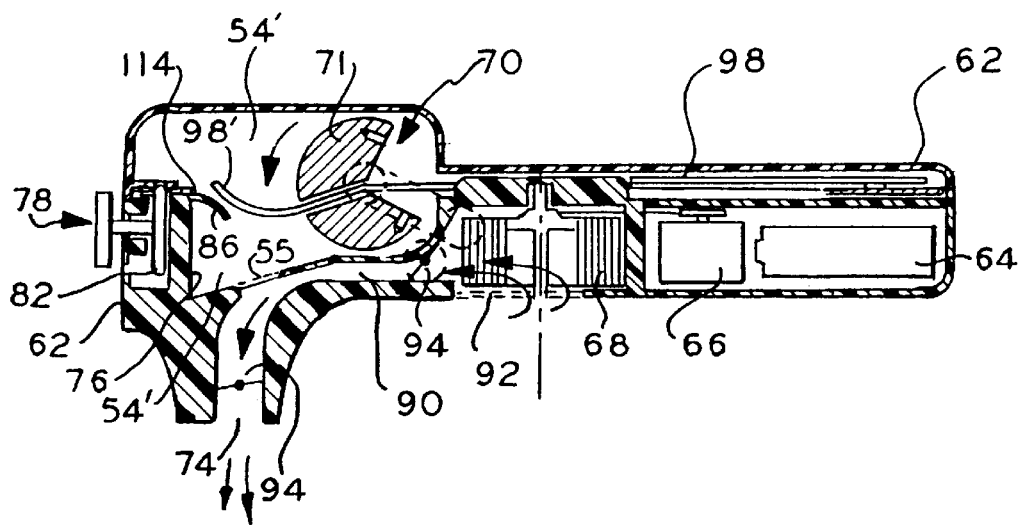

This action bends the flat resilient member 86 and the aligned fingers accordingly relative to the support 76 as shown, FIG. 5. In the alternative, the member 86 may be rigid. The disc 98 fingers are bent downwardly from the upper plane surface of the support 76 and the plane of disc 98, causing the aligned fingers 102 and 112 to break their bonds with each other by a relative sliding shearing action and to break the bond between disc 112 and ring 114 by the relative shear sliding caused by the bending action. The pin 84 keeps the ring 118 periphery 116 secured to the support 76 as the cam 71 rotates.

Figure 6:
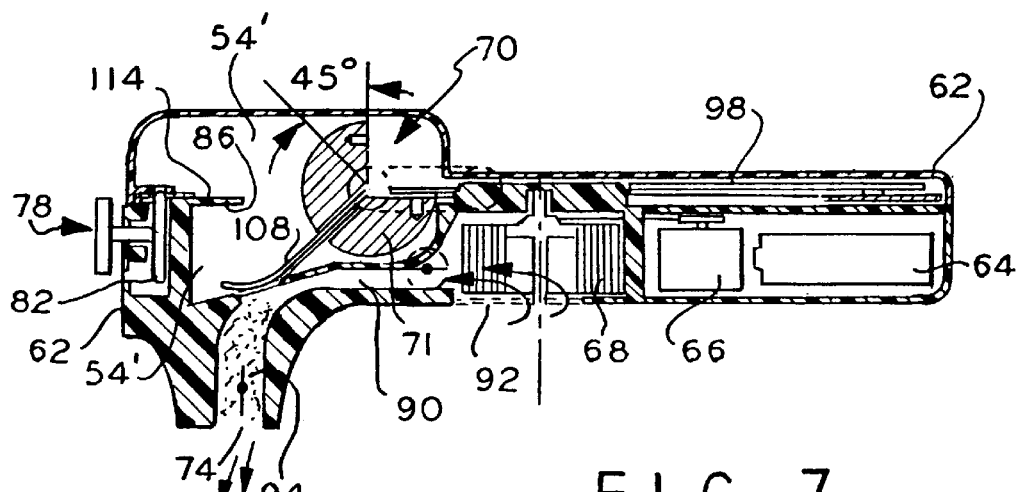

In FIG. 6, as the fingers 102 and 112 continue to rotate in response to rotation of the cam 71, the fingers 102 and 112 snap free of the bonds and slide over and past the fingers 118 of the ring 114 and the member 86. The spacer disc 108 retains the selected dosage 104 in place on the corresponding finger 102 as the mating ring finger 118 slides over the spacer disc 108. The resilient retention of the tips of the fingers 102 and 112 overlapping the member 86 and ring 114 finger creates a snap action of the fingers as the fingers rotate in response to further rotation of the cam 71, FIG. 6.

This snap action accelerates the substrate finger 102 with the dosage 104 against the bottom surface of the dispensing chamber 54' which serves as an anvil about opening 55. This creates a large impact force and rapid deceleration of the selected dosage finger 102. The momentum of the medicament during deceleration supplies energy to free the dosage from the surface 109 of the finger 102 upon the impact of the finger 102 with the anvil formed by the chamber 54' bottom surface. This momentum energy pulse causes the dosage medicament powder to be released from the disc 100. The dosage is discharged at the mouthpiece 72 port 74 as a powder cloud through the discharge opening 55. The valves 94 automatically open in response to an inhalation bolus and the concurrent air flow caused by the fan 68. The user inhales the freed powder discharged from the mouthpiece. The air inlet port 92 permits the inhaled air to draw an airstream in the direction of the arrows at the inlet port 92 through the mouthpiece 72.

The cam opening 58, FIG. 4, permits the cam 71 to rotate while flexing the fingers 102 and 112 at the slot 56. The particles readily release from the carrier substrate to provide the anticipated dosage.

Figure 7:
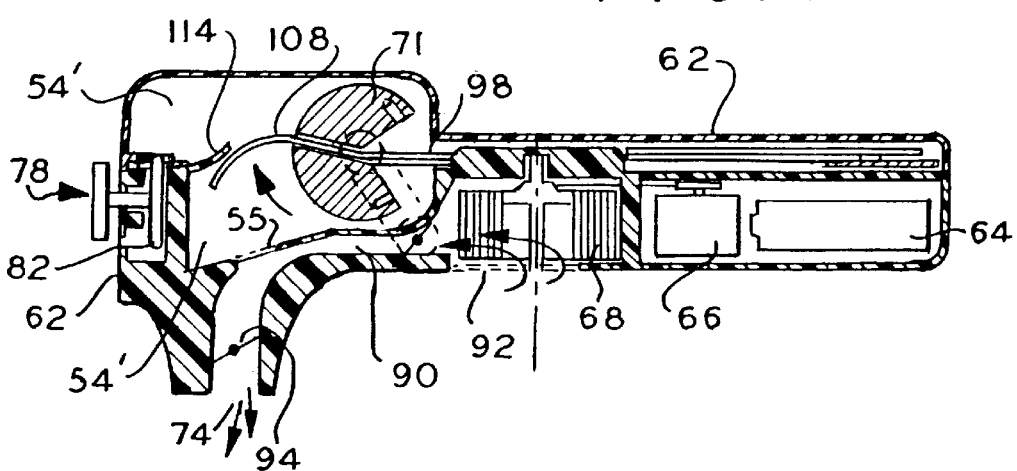

In FIG. 7, manual rotation of the cam 70 in the reverse direction returns the fingers to the disc assembly 98 plane position. The aligned ring finger 118 acts as a resilient stop and positions the fingers 102 and 112 in the quiescent spent position below the fingers 118 of the ring 114. The user may now index the next dosage for use in the next usage period at the support 76.

In the alternative, the member 86 may be rigid and arcuate having the shape as shown in FIG. 5. This arcuate shape assists in the relative shearing action of the fingers as they slide over the member 86. In the alternative, the member 86 may be omitted.

Thus, drug removal results by a momentum transfer mechanism that disrupts the drug-substrate/carrier and particle to particle bonds. Enhanced drug release is provided for the particles.

In FIGS. 8–10, further means are shown for flexing the fingers relative to the base region form imparting an energy pulse to the dosage for releasing the dosage from the finger by momentum transfer. For example, in an alternative embodiment, inhaler apparatus 122 (the housing and drive mechanism not being shown), includes a drive means for displacing a belt portion to increment the fingers, for example, such as a drive gear and motor (not shown) for rotating a reel 124 of a preferably metal dosage carrier substrate 126 carrying a medicament dosage 128 and sealed with a sealing tape 130. A sealing tape take-up reel 132, also driven by a drive gear and the motor, removes the sealing tape 130 from the substrate 126 and dosage 128 as the substrate is removed from the reel 124. A substrate take-up reel 134, driven by a further drive gear and the motor (not shown), removes the substrate from the reel 124. The reels may be part of a cartridge or cassette (the housing of which is not shown). The drive gears and circuitry for operating this system need not be shown because they are within the skill of those of ordinary skill.

In FIG. 9, the substrate 126 comprises a plurality of trapezoidal (or in the alternative triangular) fingers 136 and a continuous longitudinal extending belt 138. The dosage 128 is deposited on the free ends of the carrier fingers 136. The carrier substrate 126 preferably comprise metal leaf spring material. The fingers 136 extend transversely from the belt 138.

A clamp and dosage removing assembly 140 receives the substrate 126 and a selected dosage 128. The assembly 140 includes a clamp 141 for clamping the belt 138 next adjacent to the finger 136' in the assembly 140. The clamp 141 may comprise a slotted structure for receiving the belt 138 and prevent the belt 138 in the clamp 141 from displacing in a direction normal to the substrate (and normal to the drawing paper in FIG. 9).

The clamping assembly 140 includes an actuator 142, FIG. 9. The actuator includes a drive 143 which selectively rotates a pin 144 whose tip 144' underlies the tip of the finger 136' located within the clamp assembly 140. The pin 144 may also underlie the dosage 128' on the finger 136'. As the pin 144 is rotated, FIG. 10, it also rotates the finger 136' tip and the associated dosage 128'. As the pin 144 rotates eventually it will release the finger 136' because they rotate in opposite directions 143 and 143' (The rotated finger and pin being shown in phantom). This relative rotation permits the finger 136' when released from the pin 144 to snap back to its quiescent position shown in solid line. This snapping action causes the dosage to be displaced from the substrate by momentum transfer. While the dosage 128 is shown on a side of the finger 136 opposite the pin 144 by way of illustration, they may be on the same side in the alternative.

Figure 12:
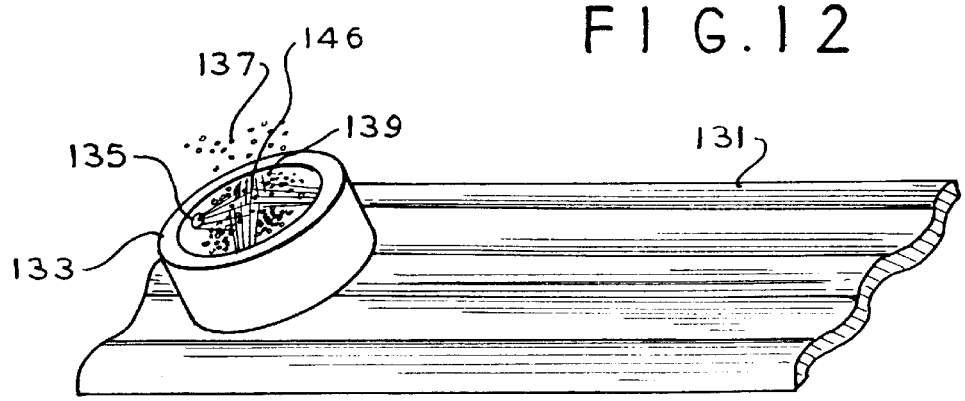
Figure 13:
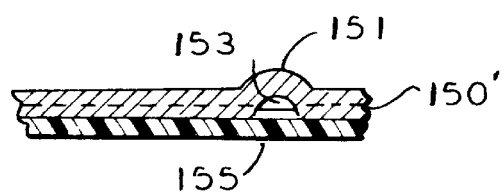

FIG. 12 illustrates an alternative carrier substrate 131 which is formed of corrugated metal leaf spring with the corrugations running along the length of the fingers of the substrate such as the substrate 126, FIG. 9, for example, or the fingers of the disc substrate 100, FIGS. 3 and 3a. The substrate is made stiffer by the corrugations without increasing the mass of the substrate. This increases the substrate acceleration for a corresponding smaller displacement of the finger. When the fingers 136 of FIG. 8, when corrugated, snap, they snap with increased acceleration over a shorter distance which further enhances the momentum energy transfer discharge of the dosage free of the substrate. The same occurs with the embodiment of FIGS. 3 and 3a.

In addition, in FIG. 12, further means for imparting an energy pulse may be provided. For example, a cylindrical hollow core preferably metal anvil 133 having a central opening 135 is positioned to receive the returning snapped finger acting as a stop for the finger in its normal quiescent position. The anvil 133, for example, in FIG. 1, may be attached to housing half 62" over opening 55. For example, the anvil 133 may be a molded integral portion of the housing half 62". The anvil 133 central opening 135 receives the released dosage from the substrate and disperses the particles into a cloud due to the momentum transfer forces. When the corrugated snapped finger substrate 131 impacts the anvil 133, FIG. 12, the dosage is flung free to the substrate as a dispersed particle cloud 137.

Means may be provided for creating an air jet stream through a channel to disintegrate aggregations. For example, the anvil 133 may have conduits 139 or channels interior to the opening 135 therethrough. When a person inhales, the breath bolus creates an air stream 146 through each of the conduits 139 which help break up agglomerates of the drug particles. This is particularly useful for large dosage deposits.

Figure 11:
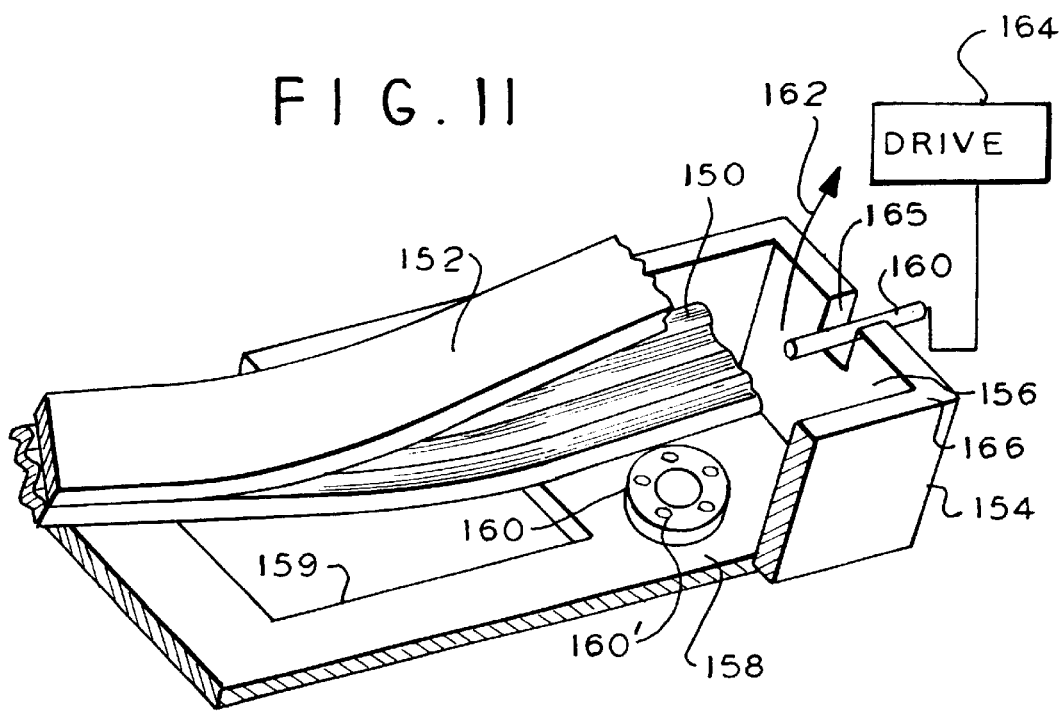

In FIG. 11, an alternative embodiment, means for flexing a finger, for snap releasing a finger and for imparting an energy pulse, for example, employing a corrugate finger, includes a corrugated preferably metal stainless steel leaf spring finger 150 extending from a base region not shown, for example, on a disc dosage carrier substrate as described previously. An overlying second resilient spring finger 152 also extends from the base region. The finger 152 is flat with no openings therethrough. The finger 152 is of different material than finger 150 and has less resiliency than finger 150,i.e., is not as stiff and, therefore, accelerates from a bent position at a slower rate than the finger 150 for a given deflection.

The finger 152 extends for the length of finger 150 and preferably overlies the entire finger 150. A channel member 154 defines a channel region 156 which receives the fingers 150 and 152 in their normal quiescent position (not shown in this figure) and flexed configuration. This quiescent position is parallel to the member 154 bottom wall 158 at the bottom of the channel region 156. Wall 158 has a through opening 159 to permit excess flow of air created by the finger 150 to exit the channel region when the flexed finger 150 returns to the flat state. This opening is then covered by the spring finger 150 when it returns to its quiescent position.

Also anvil 160 is located at the channel region bottom and secured to wall 158. Anvil 160 may be similar to the anvil 133 as described above in connection with FIG. 12.

An actuating pin 160 is rotated in direction 162 by a drive 164. The pin 160 passes through a slot 165 in the channel member 154 rear wall 166. The finger 152 has a spring constant different than that of the finger 150. This different spring constant is such that finger 150 snaps back to its original quiescent position at a higher acceleration rate than finger 152.

In operation, the pin 160 is selectively rotated in direction 162. The tip of the pin 160 (or other shaped element) is beneath the spring fingers 150 and 152, or in the alternative, beneath just finger 150 at its end tip region. As the pin is rotated upwardly in direction 162 the fingers 150 and 152 are flexed upwardly bending them about a pivot at which the fingers are secured to a base member (not shown).

The corrugated finger 150 is stiffer than finger 152 and accelerates at a higher rate, hitting the anvil 160 first. The slower moving finger 152 lags the finger 150 during the return motion to the quiescent state. The finger 152 acts as an air pump within the channel region 156 which closely receives the finger 152 and creates an air flow toward the anvil 160. This air flow creates air streams through the apertures 160' in the anvil to break up aggregations of the powder dosage. This action insures that the dosage is in proper particle size format when inhaled maximizing its effectiveness. In FIG. 11 it should be appreciated that the dosage is on the underside of the corrugated finger 150 and is not shown. The spring 150 causes its created air flow to flow through the opening 159.

The corrugated springs may form stand alone components or joined together by or formed as a tape or formed into a pin wheel or disc for purposes of advancing dosages into an inhalation chamber. Once in the chamber, the deflected spring is released so that the drug is accelerated and leads the advancing spring end. At the peak velocity, the free end of the spring strikes the rigid anvil 160 and is rapidly decelerated. The impact with the anvil 160 and the rapid deceleration result in forces sufficiently high to release the individual and aggregate drug particles from the spring by momentum transfer forming a powder cloud. Aggregate particles are disrupted once they leave the substrate by the jets of gas through which the dislodged particles must pass. Due to rapid motion of the aggregates through the jets, a timed jet is provided that represents only a fraction of the inhaled bolus. This permits aggregate disruption without disruption to the patient's breathing pattern.

In a further embodiment, in the alternative, means for flexing a finger, for snap releasing a finger and for imparting an energy pulse, for example whereby corrugations in the region of the deposited dosage may be replaced with cupped shaped substrates, such as illustrated by fingers 102', FIG. **3*b***, for example, provide the desired stiffness and flexibility in a manner similar to that of the corrugated substrate. This configuration provides additional stiffness without increasing the mass and results in more rapid deceleration and improved drug release. This provides the desired energy pulse to the substrate to release the drug rapidly.

In the alternative, means for creating an air jet stream may include a piston, not shown, which may receive the impact of the spring 152 to create an air flow through the anvil 160 apertures 160'.

In FIG. 13, a corrugated substrate 150' has pockets 151 in each of which is disposed a medicament powder dosage 153. A sealing tape 155 seals the dosages in the pockets 151. The sealing tape must then be selectively removed prior to release of the dosage. The tape does not contact the dosage so as to not remove any of the dosage when the tape is removed.

It should be understood that the transfer of the dosages in the various embodiments is by imparting an energy pulse to the powder on the carrier substrate by deflecting the carrier substrate and the subsequent rapid deceleration of the substrate. Upon resilient return of the deflected substrate, it impacts a stationary anvil or its equivalent imparting a momentum or inertial energy pulse to the moving dosage. This energy pulse transfers the dosage by way of its momentum energy induced when its support substrate rapidly decelerates upon impact with a stationary object.

This is to be distinguished from impact transfer in the prior art attributed to shock energy imparted to a relatively stationary substrate. The impact shock waves travel through the substrate to the particles thereon, releasing the particles by a direct impact force on the stationary particles. This is different than momentum transfer in which the momentum inertial energy in the moving dosage is what separates the dosage from the rapidly decelerating carrier substrate. In contrast, shock waves impart motion to the otherwise stationary powder carried on the substrate. The shock waves incident on the powder impel the powder from the carrier substrate.

The separation mechanism forces are different in the two arrangements. One is an impelling force similar to a golf club hitting a stationary ball and the other is inertial wherein the moving object tends to remain in motion when its carrier suddenly ceases motion as in a catapult.

In FIG. 14, means for flexing a finger, for snap releasing a finger and for imparting an energy pulse, for example in a further embodiment of a cassette for a tape substrate is shown. The cassette 170, dashed lines, contains three reels 172, 174 and 176. Reel 176 stores a coil 178 of a dosage carrier substrate 180 covered with a sealing tape 182. Sealing tape 182 seals the medicament dosages 194 in blisters 195, FIG. **14*a*, formed in the substrate 180. Reel 174 takes up the sealing tape 182 into a coil, removing it from the substrate 180 exposing the dosage 194. Reel 172 takes up the substrate 180 after the dosages 194** are removed.

A hollow mouthpiece 184 for the inhaler (the remainder of which is not shown) is aligned with the dosage 194 to be dispensed. The mouthpiece 184 is adjacent to anvil 197. The anvil 197 is a flat metal plate with an aperture 199 for passing the dosage 194 therethrough. The anvil 197 is next to the uncovered substrate 180 and dosage 194 to be dispensed, but spaced slightly therefrom. The inhaler includes a reel drive 186 for operating the reels 172, 174 and 176.

An impact mechanism 188 includes a cantilevered spring 190 driven by a spring deflection drive 192. The drive 192 may be a rotating pin or element as discussed above in the embodiments of FIG. 10 or 11. A powder dosage 194 deposited by a deposition technique as disclosed, for example, in the aforementioned applications and patents in the introductory portion is on the carrier substrate 180 blister 195 at a dose release position 191 aligned with the spring 190. The spring 190 has an aperture 193 for receiving and seating the blister 195 therein. The aperture 193 aligns the dosage 194 at the anvil aperture 199.

Drive 192 deflects the spring 190 and carrier substrate which impacts the dosage carrying substrate 180 against the anvil 197. The impacted substrate 180 imparts a momentum transfer motion to the dosage 194. This action releases the dosage into a powder cloud upon impact of the substrate with the anvil. The cloud is inhaled by the user via the mouthpiece 184.

Figure 16:
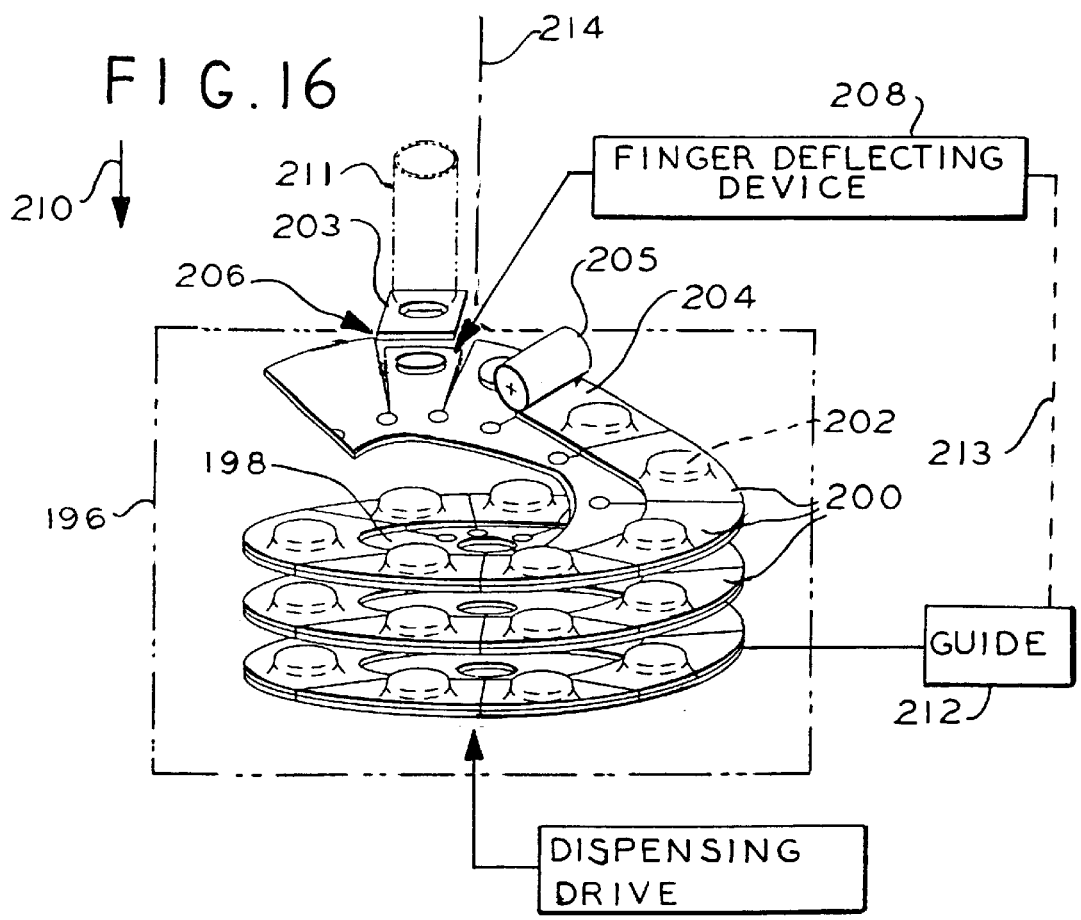
FIG. 16 is a diagrammatic isometric view of a spiral embodiment of an impact inhaler medicament dosage delivery system.
Figure 17:
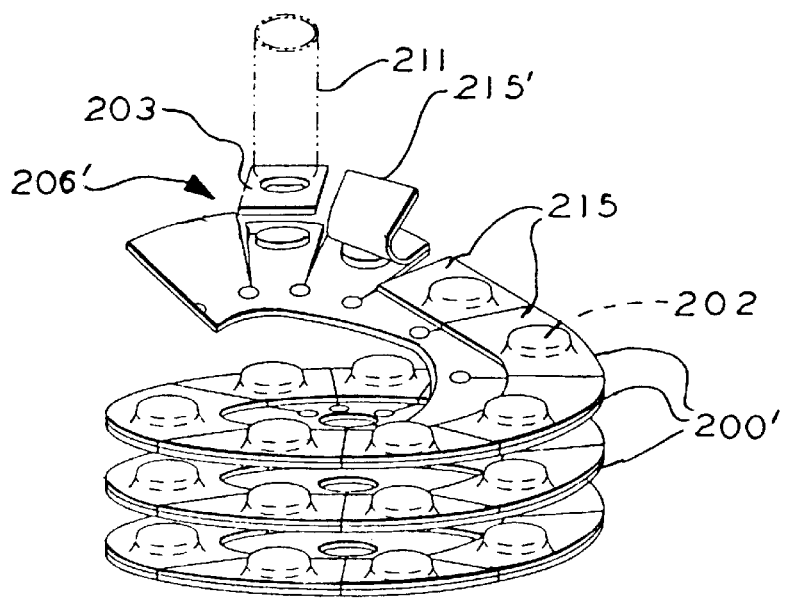
FIG. 17 is a diagrammatic isometric view of a second embodiment of a spiral impact inhaler medicament dosage delivery system.

In FIG. 15, means for flexing a finger, for snap releasing a finger and for imparting an energy pulse, for example, embodied in a reel drive and deflection drive (not shown) as described in connection with FIG. 14 is also employed. Most of the elements in FIG. 15 are the same or similar to those in FIG. 14. The difference is that the substrate 180' has a blister pocket 195', FIG. 15*a*, for receiving a dosage 194' surrounded by an annular depression 189. The sealing tape 187 has a score over each blister pocket 195'. The anvil 177 is a flat plate with an annular outer depending ring rib 179 that mates in the depression 189. The anvil has a central aperture 181 for receiving the dosage therethrough. As a result, the sealing tape rides directly on and over the anvil 177 and the dosage carrier substrates rides directly on and over the spring 190'. The sealing tape 187 and substrate 180' are coiled and taken up in a take-up rewind reel 172'. In FIG. 14, the reel 172 only takes up and coils the substrate 180.

In operation, during an index cycle, the web of the carrier substrate, dosage and sealing tape is advanced. The blister pocket 195' is inserted into the leaf spring 190' aperture 193', loaded and fired against the anvil 177. The anvil 177 outer ring rib 179 forces the cover sealing tape 187 to rupture along the score 185, FIG. 15*b*, and be pulled into the outer ring depression 189 of the dosage substrate exposing the powdered dosage 194'. The spring 190' continues in its travel and the impact with the anvil 177 releases the dosage 194', FIG. 15*b*, from the substrate 180'.

In FIG. 16, means for flexing a finger, for snap releasing a finger and for imparting an energy pulse, for example, is embodied in a cartridge 196, which is employed with an inhaler (not shown). The cartridge comprises a central core 198 and a spiral array of cantilevered spring fingers 200. Included is a core member drive means for selectively rotating the core about an axis to locate each finger at a given angular position about the axis. The fingers 200 extend radially outwardly from the core 198 and may be molded thermoplastic or metal. Each finger 200 includes a deposited medicament powder dosage 202. The dosages are deposited in any known technique as discussed hereinabove. The dosages are sealed with a sealing tape 204. The dosages may be deposited in a pocket in the finger dosage carrier substrate or the sealing tape may have performed pockets for receiving the dosage so there is no contact of the tape with the powdered dosage. The tape 204 is removed by reel 205 with a reel take-up drive (not shown) selectively exposing the dosages one at a time as they are to be dispensed.

By way of example, the fingers 200 may be supplied as a strip with the dosages thereon. The core 198 in this case has a spiral groove (not shown) in its side wall. The finger strip is then inserted in the spiral groove. The core 198 is rotatable about two spindles (not shown) at opposite axial ends of the core.

The take-up reel 205 removes the sealing tape 204 over the dosages 202 and fingers 200 as the dosages are rotated to a dispensing position 206 at a given angular position relative to the core 198.

Means are at an angular position for displacing a finger along the axis, for example, a finger deflecting device 208 deflects the fingers 200 one at a time after the selected finger is rotated to the dispensing position 206. Such as deflecting device may be as shown in FIGS. 10 and 11, for example. An apertured flat anvil 203 is fixed over and adjacent to the finger at position 206. As the core is rotated, the spiral path of the fingers 200 containing a dosage to be dispensed displaces relatively downwardly in axial direction 210 at position 206.

A guide 212 is connected to the finger deflecting device 208 represented by the dashed line 213 and slides in direction 210 in a channel in the inhaler housing (not shown). The guide axially positions the finger deflecting device as the selected dosage and finger relatively displace axially as the spiral is rotated. The guide 212 engages the spring fingers at a location spaced from the deflecting device and associated deflected finger. The guide 212 is positioned axially in direction 210 as the fingers are rotated about axis 214. The guide 212 for example has a slot (not shown) which receives the edges of the fingers as the fingers are rotated about axis 214. The fingers 200 hold the guide 212 in the axial position. An axial channel (not shown) in the housing holds the guide in its annular position 206 about the axis 214.

In operation, a user rotates the core 198 to locate a dosage and its corresponding carrier finger to the desired axial and angular position relative to axis 214 at angular position 206 of the deflecting device 208. The sealing tape 204 is peeled free of the dosage as the core is rotated by take up reel 205. A detent device, e.g., a spring loaded ball attached to the housing (not shown) and a depression in the core 198 corresponding to each finger 200 angular position about axis 214, may provide such a position for a manually rotatable core.

Manually operated finger 200 deflecting device 208 deflects the selected dosage carrier finger 200 at position 206 downwardly direction 210. When the displaced finger 200 is released it snaps back against the anvil 203 carried by the device 208, releasing the selected dosage 202 in a manner described previously by momentum transfer. The released powder cloud is inhaled via mouthpiece 218.

The mouthpiece is schematically illustrated as having a vertical orientation along axis 214. In practice, the mouthpiece may be horizontal transverse to the axis 214. The mouthpiece may be coupled to a channel (not shown) in the housing interior side wall for flowing the released powder cloud to the mouthpiece at the edge of the spiral substrate fingers at position 206.

A fan and/or additional air flow paths for providing an auxiliary air flow to assist in exhausting the powder cloud during inhalation may also be provided as in FIG. 1 for this and the embodiments of FIGS. 14 and 15. The reel 205 is also coupled to the guide 212 for displacement therewith in the axial direction. A mouthpiece 211 receives the discharged powdered dosage.

In FIG. 17, means for flexing a finger, for snap releasing a finger and for imparting an energy pulse, for example, is shown in an embodiment similar to that of FIG. 16 employing a spiral dosage carrier substrate with resilient cantilevered fingers. In this embodiment all of the elements of FIG. 16 are utilized except that the dosage 202 are encapsulated at each finger 200' by a discrete sealing cover sheet 215. The sealing cover sheet preferably has a pocket for receiving the dosage. In this case the take-up reel 205 of FIG. 16 is not utilized. In its place, a device (not shown) peels back the discrete cover sheet 215' next prior to the deposition position 206'.

Figure 18:
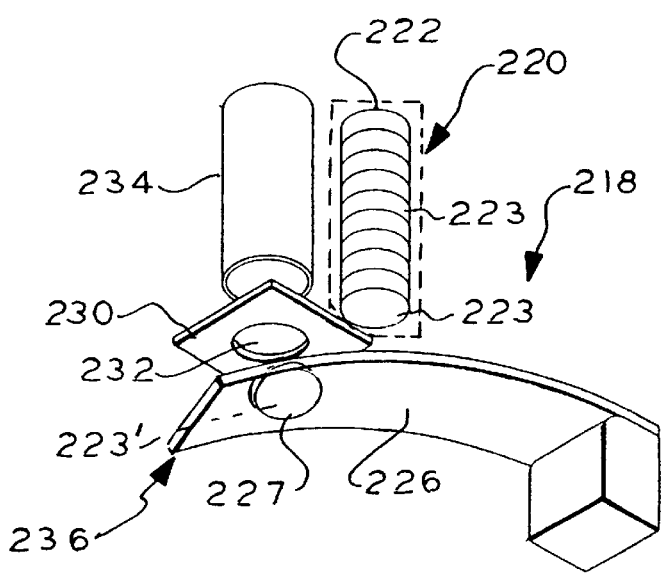
FIG. 18 is an isometric diagrammatic view of a further embodiment of an impact inhaler medicament dosage delivery system employing stacked dosage packs.
Figure 18A:
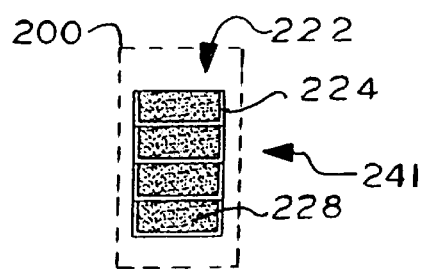
FIG. 18a is a side sectional elevation view of the stack of packs employed in the FIG. 18 embodiment.

In FIGS. 18 and 18a, means for flexing a finger, for snap releasing a finger and for imparting an energy pulse, for example, is shown in a further embodiment of an inhaler dispenser 218, which includes a housing (not shown) having a chamber for receiving a cartridge 200. The cartridge 200 comprises a stack 222 of dosage packs 223. Each pack 223 comprises a circular cylindrical (or other shapes) dosage wafer blister type substrate 224. The substrates 224 each comprise a thermoplastic blister forming a pocket for the powdered dosage 228. The substrates may be any conventional material, and preferably formed thermoplastic. The powdered medicament dosage 228 is deposited in the pocket of each substrate 224 by any known process as discussed above.

The cartridge 220, which may be any convenient packaging for the packs is inserted into the inhaler chamber. During an index cycle, the lead pack 223' is separated from the cartridge and stack by a dispensing device (not shown) and placed on the cantilevered dosage carrier leaf spring 226 in a mating pocket 227 or aperture (not shown) in the spring 226. A flat anvil 230, for example metal or plastic, has a dosage receiving aperture 232. A mouthpiece 234 is adjacent to the aperture 232 for receiving a powder cloud dosage.

An impact mechanism including a spring deflection drive (not shown) is at station 236 for deflecting the spring 226 and impacting the dosage 228 and substrate 224 against the anvil 230 to impart the desired energy pulse to release the dosage. The anvil 230 aperture 232 is smaller than the substrate so the dosage substrate will impact against the anvil when the spring is directed toward the anvil 230.

The deflection drive (not shown) selectively rotates and snap releases the spring 226. Drive 238 may be manual or electrically operated. The released spring 226 impacts the deflected substrate 224' against the anvil 230 on a side facing the spring 226 to release the dosage by momentum transfer. The released dosage passes through the anvil aperture 232 into the mouthpiece 234. The relative orientations and positions are given by way of illustration and may differ from that shown in a given implementation. After the dosage is released, the empty pack 223' substrate 224 is displaced to a storage location (not shown) by a displacement device (not shown).

Figure 19:
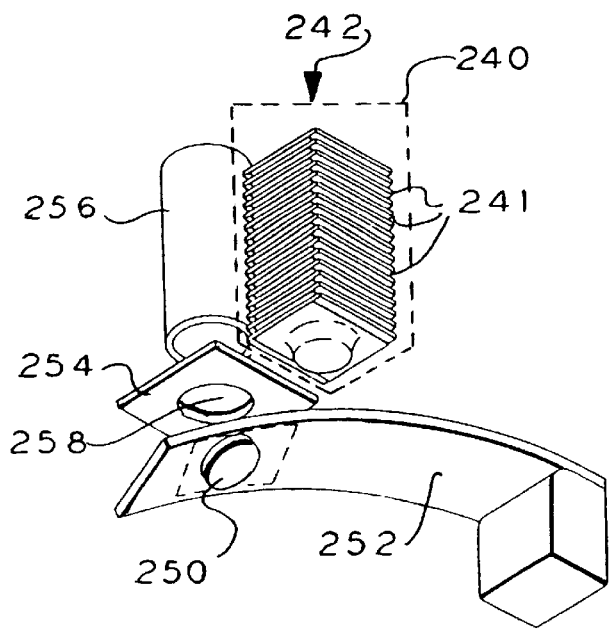
FIG. 19 is an isometric diagrammatic view of a second embodiment of an impact inhaler medicament dosage delivery system employing stacked substrates and medicament dosages.
Figure 19A:
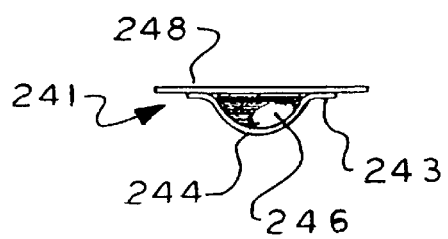
FIG. 19a is a side sectional elevation view of the each substrate of the stack of dosage packs employed in the FIG. 19 embodiment.

In FIGS. 19 and 19a, means for flexing a finger, for snap releasing a finger and for imparting an energy pulse, for example, is shown in a further embodiment of a cartridge dispenser for stacked substrates which includes a cartridge 240 mounted in an inhaler chamber (not shown). Cartridge 240 is any convenient packaging for stacked substrates which comprises a stack 242 of separate substrate-dosage packs 241. Each pack 241 comprises like discrete formed thermoplastic blister type substrates 243 each having a dosage 246 receiving pocket 244. A medicament dosage 246 is in each pocket. The dosages 246 are sealed by a discrete sealing cover 248 over each substrate 242 forming the completed pack 241.

A flat anvil 254 is adjacent to the mouthpiece 256. The anvil 254 has a dosage receiving aperture 258. The anvil is secured fixed to the inhaler housing (not shown) as in the prior embodiments discussed above herein.

Means are provided for selectively placing successive dosages and dosage substrates on a carrier such as during indexing, when the cover 248 is removed from the substrate 243 by a device (not shown). The exposed dosage 246 and substrate 243 of the pack 241 are then placed in a pocket 250 in dosage carrier spring 252 by a mechanism (not shown). Mouthpiece 256 is at the dosage dispensing station. The spring 252 and carried dosage are displaced by a deflection device (not shown) which deflects the spring to the position shown in the Figure with the substrate and dosage thereon. The displaced spring upon snap release by the deflection device, will impact the anvil 254, and release the dosage 246 from the substrate 243. The substrate 243 is smaller than the aperture 258 in the anvil so that the anvil restrains the substrate upon impact. This action provides momentum transfer energy to the dosage which forms a powder cloud that is dispensed through the mouthpiece 256.

It will occur to one of ordinary skill that modifications may be made to the disclosed embodiments without departing from the scope of the invention as defined in the appended claims. The description given herein is by way of illustration and not limitation. For example, the shape of the fingers and the particular actuating mechanisms are by way of example. Numerous other actuating mechanisms may be provided for flexing a spring finger to impart an energy pulse to a dosage on a substrate to transfer the dosage by momentum transfer forces.

What is claimed is:

1. A medicament powder delivery device comprising:
    a carrier having at least a flexible portion including a dosage carrier finger resiliently extending from a base region on which finger is a discrete medicament dosage; and
    means for flexing the finger relative to the base region and snap releasing the flexed finger relative to the base region for imparting an energy pulse to the dosage for releasing the dosage from the finger by momentum transfer.

2. The device of claim 1 including a body with a cavity for receiving the flexible portion and the means for imparting, the device including an anvil with a bore therethrough fixed to the body in the cavity for impact receiving the snap released finger, the bore for receiving said released dosage, and including means for causing said finger to resiliently impact said anvil to rapidly decelerate the finger to provide said momentum transfer to the dosage.

3. The device of claim 2 wherein said anvil including at least one channel, further including means for creating an air jet stream through said at least one channel to disintegrate aggregations of said dosage during said impact.

4. The device of claim 1 wherein the finger is corrugated.

5. The device of claim 3 wherein the carrier finger extends in a given direction from the base region, the finger having corrugations extending along said direction.

6. The device of claim 3 wherein the means for creating said jet stream includes a further resilient finger overlying the carrier finger for initial resilient displacement coincident with initial displacement of the carrier finger, said displaced fingers for snap release in a second displacement, said further finger for creating said air jet stream during said second displacement.

7. The device of claim 6 wherein the further finger has a different relaxation time than the carrier finger so as to accelerate slower than the carrier finger upon said snap release.

8. The device of claim 1 wherein the carrier includes a first disc with a plurality of radially extending fingers, a dosage on each finger, and the means for imparting comprises cam means for snap flexing a selected finger to release the dosage on the selected finger.

9. The device of claim 8 including index means for indexing the selected finger to a medicament release position for snap flexing the selected finger by said cam means.

10. The device of claim 9 wherein the first disc includes a dosage carrier disc with a plurality of first fingers each carrying a dosage, a spacer disc overlying the carrier disc with a plurality of second fingers overlying and corresponding to the first fingers and a ring with index holes and a third plurality of fingers over lying and corresponding to the first and second fingers, said spacer disc being bonded to the carrier disc and ring, said indexing means for selectively engaging said ring index holes.

11. The device of claim 10 wherein the cam means flexes the first and second fingers past the third fingers.

12. The device of claim 1 wherein the carrier comprises a belt portion with a plurality of said fingers extending transversely from the belt portion, each said fingers having a separate dosage and arranged for selective resilient displacement relative to said belt portion.

13. The device of claim 12 further including drive means for displacing said belt portion to increment said fingers sequentially to a dosage release position.

14. The device of claim 12 wherein the means for imparting includes a clamp for clamping the belt portion adjacent to a given finger and a deflecting member for selectively flexing and snap releasing the selected given flexed finger relative to the belt portion.

15. The device of claim 1 wherein said finger is for receiving a dosage and dosage substrate from a plurality of dosages and dosage substrates in a stack aligned one over another, further including means for selectively placing successive dosages and dosage substrates on said carrier, said means for imparting including means for snap deflecting said finger against an anvil.

16. The device of claim 1 wherein the carrier comprises an element having a plurality of said fingers, said dosage comprising a dosage on each finger, said means for flexing including a finger deflection member adjacent to said element for momentarily bending and deflecting a selected finger to momentum transfer release a selected dosage from the finger upon release of the deflected finger.

17. The device of claim 16 including means for selectively aligning successive dosages on said element to said deflection member.

18. The device of claim 16 including a core member rotatable about an axis, said element comprising an array of said fingers radially extending from the core member about the core member in a spiral about said axis, said device including means for selectively aligning and deflecting each said finger to snap release a selected dosage from the selected finger by said momentum transfer.

19. The device of claim 1 further including:
a cartridge containing said carrier, said carrier comprising a plurality of said fingers;
the medicament dosage comprising a dry powder in a discrete location on each finger;
a housing for receiving the cartridge; and
the means for flexing for momentarily deflecting a selected finger to accelerate and rapidly decelerate the selected finger for said imparting;
the cartridge comprising a cylindrical core member, said plurality of fingers extending radially from the cylindrical core member in a spiral array, said means for flexing including anvil means for said rapid deceleration of the selected flexed finger.

20. The device of claim 19 wherein the means for selectively deflecting includes a core member drive means for selectively rotating the core member about an axis to locate each finger at a given angular and axial position about the axis and a finger deflecting device at said given position, said selectively deflecting means including means at said angular position for displacing the finger along said axis.

21. A dry powder deliver device comprising:
a cartridge containing at least one dosage carrier substrate;
a dry powder in an array of discrete locations on the at least one substrate;
a housing for receiving the cartridge; and
means for momentarily deflecting the carrier substrate to accelerate and rapidly decelerate the substrate to momentum transfer and discharge the powder from the substrate at a selected location;
the cartridge comprises a plurality of reels with the carrier substrate suspended between the reels, the means for deflecting comprising a cantilevered spring member for said momentarily deflecting the carrier substrate between said reels and a fixed anvil for impact receiving the deflected substrate.

22. A dry powder delivery device comprising:
a cartridge containing at least one dosage carrier substrate;
a dry powder in an array of discrete locations on the at least one substrate;
a housing for receiving the cartridge; and
means for momentarily deflecting the carrier substrate to accelerate and rapidly decelerate the substrate to momentum transfer and discharge the powder from the substrate at a selected location;
the cartridge comprising a disc having a plurality of radially outwardly extending fingers, each finger having a dosage thereon and the means for deflecting including means for selectively deflecting each said finger.

23. A dry powder delivery device comprising:
a cartridge containing at least one dosage carrier substrate;
a dry powder in an array of discrete locations on the at least one substrate;
a housing for receiving the cartridge; and
means for momentarily deflecting the carrier substrate to accelerate and rapidly decelerate the substrate to momentum transfer and discharge the powder from the substrate at a selected location;
the cartridge comprising a stack of medicament dosages each on a discrete substrate, a spring for receiving a selected dosage on a substrate from the stack, said means for deflecting for selectively deflecting each substrate in a sequence.

24. A dry powder delivery device comprising:
a cartridge containing at least one dosage carrier substrate;
a dry powder in an array of discrete locations on the at least one substrate;

a housing for receiving the cartridge; and means for momentarily deflecting the carrier substrate to accelerate and rapidly decelerate the substrate to momentum transfer and discharge the powder from the substrate at a selected location;

the cartridge comprising a member having a base and a linear array of fingers extending from the base, each finger being flexible relative to the base and including a medicament powder dosage, said means for deflecting for selectively deflecting each finger in a sequence.

25. The device of claim 24 wherein the fingers are rectangular and parallel.

26. The device of claim 24 wherein the fingers are triangular and parallel.

27. The device of claim 24 wherein the at least one substrate has a plurality of depressions each containing a separate powder dosage and a sealing tape bonded to the substrate over the depressions and spaced from the dosages.

* * * * *